United States Patent [19]
Cohen et al.

[11] Patent Number: 5,795,288
[45] Date of Patent: Aug. 18, 1998

[54] APPARATUS WITH VALVE FOR TREATING INCONTINENCE

[76] Inventors: Kenneth L. Cohen, 9 Bishop Dr., Woodbridge, Conn. 06525; Dennis J. Hanlon, 15 Morris Rd., East Haven, Conn. 06513

[21] Appl. No.: 694,331

[22] Filed: Aug. 8, 1996

[51] Int. Cl.⁶ ............................................. A61F 2/00
[52] U.S. Cl. ................... 600/29; 600/30; 128/DIG. 25; 604/327; 604/329
[58] Field of Search ............... 600/29–32; 128/DIG. 25, 128/834, 835, 836; 604/327, 328, 329

[56] References Cited

U.S. PATENT DOCUMENTS

| | | |
|---|---|---|
| 2,616,429 | 11/1952 | Merenlender . |
| 3,331,371 | 7/1967 | Rocchi et al. . |
| 3,459,175 | 8/1969 | Miller . |
| 3,503,400 | 3/1970 | Osthagen . |
| 3,646,929 | 3/1972 | Bonnar . |
| 3,797,478 | 3/1974 | Walsh et al. . |
| 3,811,448 | 5/1974 | Morton . |
| 3,811,450 | 5/1974 | Lord . |
| 3,812,841 | 5/1974 | Isaacson . |
| 3,841,304 | 10/1974 | Jones . |
| 3,854,469 | 12/1974 | Giori et al. . |
| 3,866,611 | 2/1975 | Baumrucker . |
| 3,903,894 | 9/1975 | Rosen et al. . |
| 3,939,821 | 2/1976 | Roth . |
| 4,022,216 | 5/1977 | Stevens . |
| 4,209,009 | 6/1980 | Henning . |
| 4,256,093 | 3/1981 | Helms et al. . |
| 4,350,161 | 9/1982 | Davis . |
| 4,428,365 | 1/1984 | Hakky . |
| 4,432,757 | 2/1984 | Davis, Jr. . |
| 4,457,299 | 7/1984 | Cornwell . |
| 4,553,533 | 11/1985 | Leighton . |
| 4,579,554 | 4/1986 | Glassman . |
| 4,587,954 | 5/1986 | Haber . |
| 4,610,664 | 9/1986 | Harle . |
| 4,610,665 | 9/1986 | Matsumoto et al. . |
| 4,619,245 | 10/1986 | Haber et al. . |
| 4,634,443 | 1/1987 | Haber . |
| 4,673,393 | 6/1987 | Suzuki et al. . |
| 4,682,592 | 7/1987 | Thorsgard . |
| 4,692,152 | 9/1987 | Emde . |
| 4,813,935 | 3/1989 | Haber et al. . |
| 4,846,784 | 7/1989 | Haber . |
| 4,909,785 | 3/1990 | Burton et al. . |
| 4,932,958 | 6/1990 | Reddy et al. . |
| 5,030,199 | 7/1991 | Barwick et al. . |
| 5,090,424 | 2/1992 | Simon et al. . |
| 5,112,306 | 5/1992 | Burton et al. . |
| 5,147,301 | 9/1992 | Ruvio ........................ 604/329 |
| 5,181,921 | 1/1993 | Makita et al. . |
| 5,234,409 | 8/1993 | Goldberg et al. ............ 604/96 |
| 5,344,397 | 9/1994 | Heaven et al. . |
| 5,352,182 | 10/1994 | Kalb et al. ................... 600/30 |
| 5,476,434 | 12/1995 | Kalb et al. . |
| 5,513,660 | 5/1996 | Simon et al. ................ 600/29 |

*Primary Examiner*—Jennifer Bahr
*Assistant Examiner*—Rosiland Kearney
*Attorney, Agent, or Firm*—Bachman & LaPointe, P.C.

[57] ABSTRACT

An apparatus for treating incontinence includes a substantially tubular body member having a first end and a second end and defining a flow passage, an internal seal member positioned at the first end of the body member, an external retaining member positioned at the second end, at least one member of the internal seal member and the external retaining member being moveable longitudinally with respect to the other member of the internal seal member and the retaining member, ratchet structure for longitudinally securing the at least one member relative to the other member, whereby the tubular body member can be positioned in a urethra with the seal member substantially sealingly positioned in an interior opening of the urethra and with the retaining member positioned at an exterior opening of the urethra, and a valve positioned in the flow passage for controlling flow through the flow passage.

39 Claims, 3 Drawing Sheets

APPARATUS WITH VALVE FOR TREATING INCONTINENCE

CROSS REFERENCE TO PATENT OFFICE DISCLOSURE DOCUMENT

The application is related to United States Disclosure Document No. 393030 filed Feb. 14, 1996 with the United States Patent and Trademark Office pursuant to the disclosure document program.

BACKGROUND OF THE INVENTION

The invention relates to an apparatus and method for treating incontinence, particularly in females, and especially for treating urinary incontinence.

Urinary incontinence is a common problem in women. This is in large part due to laxity of bladder support structures brought on by pregnancy and/or aging. The magnitude of this problem is evidenced by increasingly large expenditures each year on products such as incontinence diapers and other protective clothing. Surgical correction is possible in some cases, but is an invasive and costly procedure. Foley-type catheters are another solution, but require the wearing of a urine collection bag, and this type of catheter is associated with frequent infections. Urethral catheters with valves have been designed, but have not been widely used.

U.S. Pat. No. 5,352,182 to Kalb et al. is drawn to a product and method to treat female incontinence wherein the proper length of the device for a particular patient is determined on a patient-by-patient basis using a measurement device as shown in FIG. 5 of the Kalb et al. patent. Devices must apparently be manufactured in different sizes to accommodate different patients.

The manufacture of devices having various different lengths or sizes is obviously not desirable and results in increased manufacturing costs. Thus, the need remains for a device which accommodates the various different lengths needed in connection with patients having differing physiology.

Further, problems are encountered with patients who are incapable of operating an incontinence treating device and therefore require assistance from attending personnel. Known devices require complicated and time consuming steps to operate which are disadvantageous for example to an attendant caring for a number of patients.

It is clear that the need remains for an apparatus and method for treating urinary incontinence which does not require the use of collection bags, or repeated insertion and removal, which does not lead to excessive irritation and/or infection, which readily adapts to urethral measurements in individual patients, and which is readily operated for voiding of urine from the bladder when needed.

It is therefore the primary object of the present invention to provide an apparatus for treating urinary incontinence which is indwelling and easy to operate.

It is a further object of the present invention to provide an apparatus which is easily implanted by a doctor or trained medical personnel.

It is a still further object of the present invention to provide an apparatus which is reliable and inexpensive, and simple in use.

It is a further object of the present invention to provide an apparatus the use of which does not lead to irritation and/or frequent infections.

It is a still further object of the present invention to provide a method for treating urinary incontinence using an apparatus according to the present invention.

It is another object of the present invention to provide an apparatus which can easily be used by a patient or attending personnel to allow urination as desired.

It is still another object of the present invention to provide an apparatus which is readily adjustable in size, especially in length.

Other objects and advantages will appear hereinbelow.

SUMMARY OF THE INVENTION

In accordance with the present invention, the foregoing objects and advantages are readily attained.

According to the invention, an apparatus is provided for treating incontinence, which apparatus comprises a substantially tubular body member having a first end and a second end and defining a flow passage, an internal seal member positioned at the first end, an external retaining member positioned at the second end, at least one member of the internal seal member and the external retaining member being moveable longitudinally with respect to the other member of the internal seal member and the retaining member, means for longitudinally securing the at least one member relative to the other member, whereby the tubular body member can be positioned in a urethra with the seal member substantially sealingly positioned in an interior opening of the urethra and with the retaining member positioned at an exterior opening of the urethra, and valve means positioned in the flow passage for controlling flow through the flow passage.

In further accordance with invention, a method for treating incontinence is provided which method comprises the steps of providing an apparatus comprising a substantially tubular body member having a first end and a second end and defining a flow passage, an internal seal member positioned at the first end, an external retaining member positioned at the second end, at least one member of the internal seal member and the external retaining member being moveable longitudinally with respect to the other member of the internal seal member and the retaining member, means for longitudinally securing the at least one member relative to the other member, whereby the tubular body member can be positioned in a urethra with the seal member substantially sealingly positioned in an interior opening of the urethra and with the retaining member positioned at an exterior opening of the urethra, and valve means positioned in the flow passage for controlling flow through the flow passage, wherein the internal seal member is positionable between a radially expanded position and a radially withdrawn position, positioning the internal seal member in the radially withdrawn position, inserting the apparatus into a urethra with the seal member extending beyond an internal opening of the urethra, positioning the seal member in the radially expanded position, moving the external retaining member relative to the seal member to an implanted position wherein the seal member substantially sealingly engages the internal opening of the urethra and the retaining member engages the external opening of the urethra, securing the retaining member relative to the seal member in the implanted position, and selectively operating the valve means for controlling flow through the flow passage.

BRIEF DESCRIPTION OF THE DRAWINGS

A detailed description of preferred embodiments of the present invention follows, with reference to the attached drawings, wherein.

DETAILED DESCRIPTION OF THE DRAWING

The present invention relates to an apparatus for treating incontinence, and especially to an apparatus for treating incontinence in females which apparatus has a valve device for enhanced useability and which is adjustable lengthwise so as to allow manufacture of a single device which can be readily adapted for implanting in patients having widely differing physiology.

Figures 1, 1A, 4:
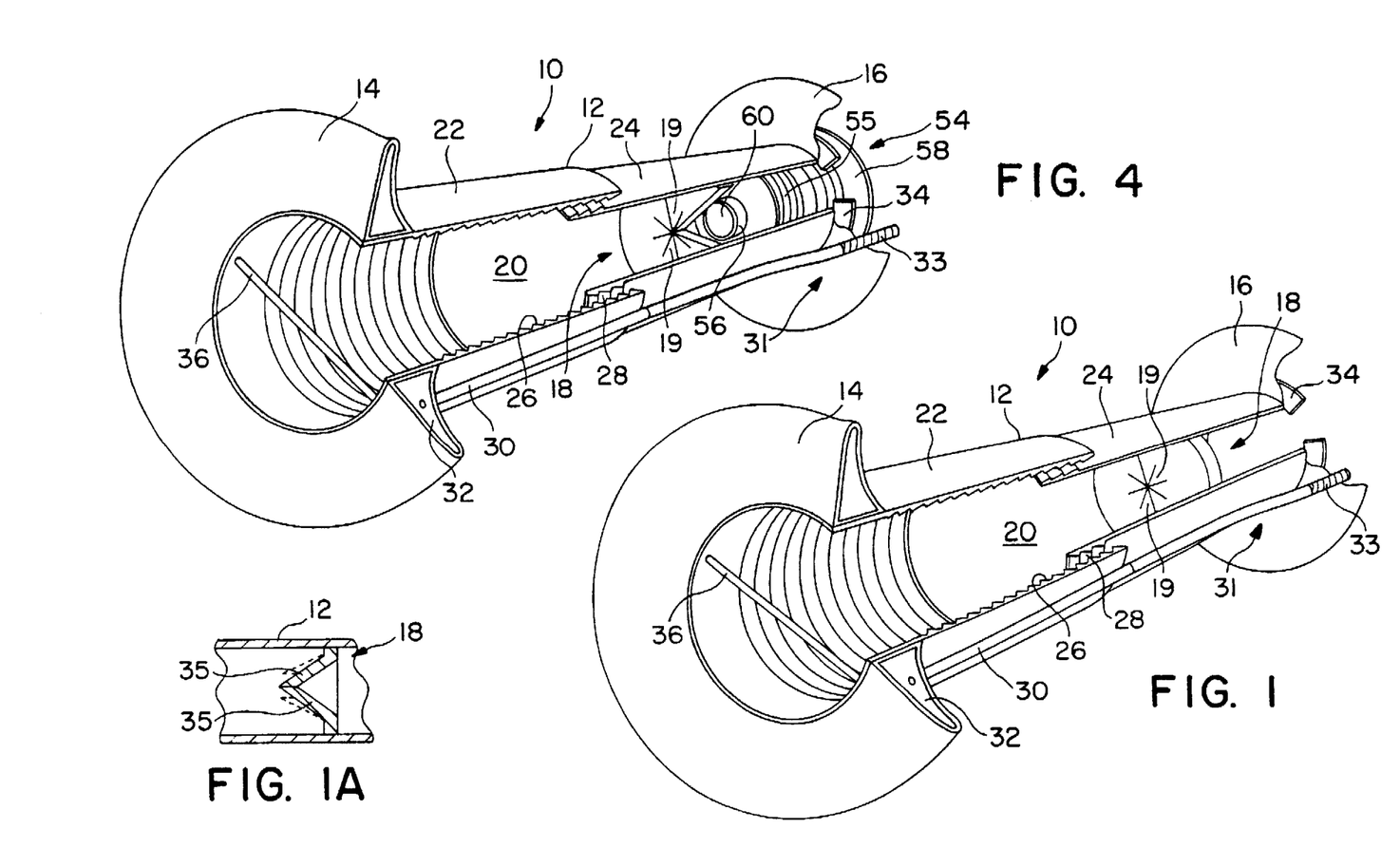
FIG. 1 is a perspective view of an apparatus in accordance with the invention.
FIG. 1A is a side schematic view of a valve member according to the invention.
FIG. 4 is a perspective view of an alternative embodiment of the invention.

Referring to FIG. 1, an apparatus according to the invention is generally referred to by reference numeral 10. As shown, apparatus 10 is a generally elongate device having a substantially tubular body member 12, a seal member 14 at one end of body member 12, a retaining member 16 at the other end of body member 12, and a valve member 18 positioned within tubular body member 12. As will be thoroughly discussed below, apparatus 10 is advantageously used for positioning within the urethra of a patient with seal member 14 substantially adjacent and sealingly associated with an internal opening of the urethra, and with retaining member 16 positioned relative to seal member 14 so as to securely engage or abut against the exterior opening of the urethra, while valve member 18 may be selectively operated to block and allow flow through tubular body member 12 as desired.

As shown in FIG. 1, body member 12 is preferably a substantially tubular structure defining an internal passage or flow passage 20, and is preferably made from a flexible and resilient material such as, for example, polyethylene, polypropylene or other plastic polymer and the like. Body member 12 in accordance with the invention preferably includes a first tubular portion 22 and a second tubular portion 24. First tubular portion 22 preferably has internal teeth or ratchets 26, while second tubular portion 24 preferably has external teeth or ratchets 28 also as shown. First and second tubular portions 22, 24, are preferably sized so that second tubular portion 24 slidably fits within first tubular portion 22. In this regard, second tubular portion may be provided preferably having an outside diameter substantially matching the inside diameter of first tubular portion 22.

Teeth 26, 28 respectively of first and second tubular portions 22, 24 are preferably adapted so as to interlock or engage against separation or outward movement of first tubular portion 22 relative to second tubular portion 24. Further, teeth 26, 28 are also preferably configured so as to readily allow inward movement of first tubular portion 22 relative to second tubular portion 24. It should be noted that the positioning of teeth 26, 28 could be reversed according to the invention so as to provide external teeth 28 on first tubular portion 22 and internal teeth 26 on second tubular portion 24, with first tubular portion 22 fitting within second tubular portion 24, all within the scope of the present invention.

Still referring to FIG. 1, seal member 14 is preferably an inflatable collar member which is positionable between a radially expanded and radially withdrawn position. In accordance with the invention, seal member 14 is preferably inflatable to a radially expanded substantially flange-shaped configuration as shown in FIG. 1. Seal member 14 is preferably connectable to a source of inflation fluid, for example through tube 30 associated lengthwise with tubular body member 12 and communicating at one end with an internal space 32 of seal member 14, and at an opposite end with a source (not shown) of fluid, for example air, for inflation of seal member 14 to the radially expanded position of FIG. 1. Tube 30 may simply be positioned adjacent an outer wall of tubular body member 12 as shown. Alternatively, tube 30 may be arranged within passage 20 defined by tubular body member 12, or within the wall thickness of tubular body member 12.

Tube 30 at end 31 thereof preferably has a self-sealing section 33 which extends through retaining member 16, preferably slidably relative to retaining member 16. Section 33 may suitably be made of a self-sealing material which substantially seals against fluids, particularly fluids used to inflate seal member 14, after removal of a penetrating object. The length of section 33 is preferably selected to allow a portion of section 33 to be trimmed away at a desired position of portion 22 relative to portion 24 so that excess material can be removed after adjusting length of apparatus 10 while retaining desired self-sealing properties.

Retaining member 16 is preferably a substantially flexible flange or collar member disposed over second tubular portion 24 as shown. In accordance with the invention, the positioning of seal member 14 on first tubular portion 22 and retaining member 16 on second tubular portion 24 advantageously provides for retaining member 16 to be movable longitudinally with respect to seal member 14 as desired. This structure advantageously provides for adjustability in length of apparatus 10 to accommodate differing urethral dimensions of various patients in accordance with the present invention and to assist in accurate implanting of the device by allowing secure positioning of seal member 14 and retaining member 16 as desired. Retaining member 16 may suitably be integrally formed with second tubular portion 24, or alternatively can be securely fixed with respect to second tubular portion 24, for example by abutment against flange 34 of second tubular portion 24.

Valve member 18 is preferably positioned as shown within passage 20 for substantially blocking flow through passage 20 as desired. Valve 18 is preferably actuable or positionable between a flow position wherein flow through valve 18 and passage 20 is allowed as desired, and a sealed or closed position wherein flow through valve 18 and passage 20 is blocked. FIG. 1 shows valve 18 mounted within second tubular portion 24. As will become apparent from a consideration of the other drawings, valve 18 could be positioned within first tubular portion 22. FIG. 1 shows valve 18 as a simple cruciate or slitted valve wherein deflection of several of the prongs 19 of valve 18 creates an opening through valve 18 and allows flow therethrough.

Referring to FIG. 1A, a cross section of an alternative embodiment of valve 18 is provided wherein valve 18 is a duck bill valve having wall portions 35 extending inwardly into contact with each other. This structure of valve 18 serves to further inhibit unwanted flow through valve 18. Wall portions 35 are biased toward the closed position shown in solid lines in FIG. 1A wherein flow through valve 18 is substantially blocked, and wall portions 35 are deflectable to an open position illustrated in dashed lines, wherein flow through valve 18 is permitted. Of course, a wide variety of alternative structure could be provided for use in accordance with the present invention, several alternative embodiments of which will be described hereinbelow.

Referring back to FIG. 1, a rod 36 may suitably be positioned, for example within passage 20 of first tubular portion 22. As will be discussed below, rod 36 serves to provide a structure which can be gripped using an instrument controlled from a position remote from tubular body member 12 so as to hold first tubular portion 22 in a desired position during movement of second tubular portion 24 and ratcheting of teeth 26 relative to teeth 28. This advantageously allows for secure handling of apparatus 10 during implantation of same.

Figure 2:
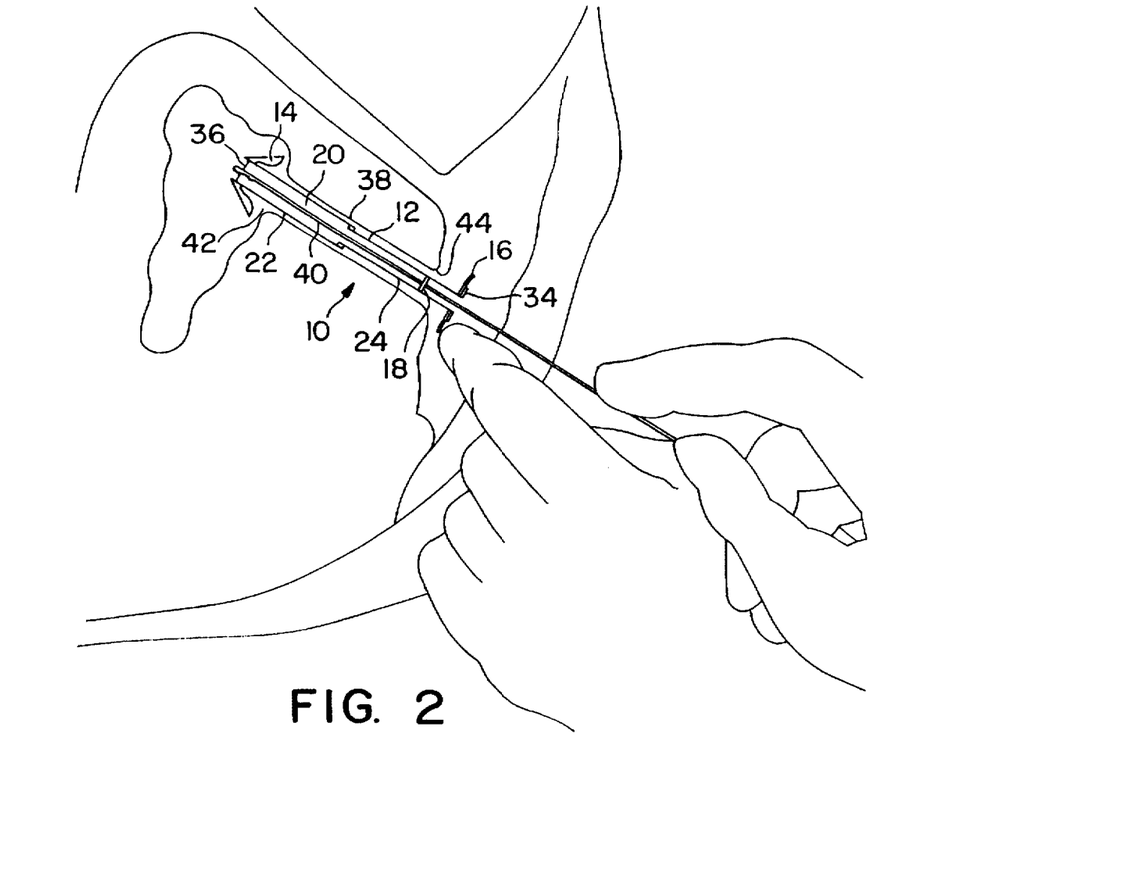
FIG. 2 is a side schematic view of an apparatus according to the invention in the process of being implanted.

Referring now to FIG. 2, the operation of seal member 14 and rod 36 during implantation of apparatus 10 will be further described. As shown in FIG. 2, apparatus 10 is advantageously suited for use in treating incontinence, especially in females, through positioning body member 12 within the urethra 38 of the patient. Apparatus 10 is implanted through a procedure wherein initially, seal member 14 is deflated so as to be positioned in a radially withdrawn position as shown in FIG. 2. An elongate instrument 40 is preferably engaged with rod 36, and apparatus 10 is inserted into urethra 38 as shown in FIG. 2 to a position wherein seal member 14 extends beyond an internal opening 42 of urethra 38. Once apparatus 10 is sufficiently inserted, seal member 14 is preferably inflated through tube 30 to an inflated and radially expanded position, and second tubular portion 24 is moved inwardly or distally while first tubular portion 22 is held in place using instrument 40, so that retaining member 16 can be positioned in close or abutting proximity with respect to external opening 44 of urethra 38. As will be readily appreciated, teeth 26, 28 ratchet together during inward movement of tubular portion 24 relative to tubular portion 22. Once second tubular portion 24 is positioned to the desired location, teeth 26, 28 advantageously serve to prevent relative movement of seal member 14 and retaining member 16 away from each other and thereby secure seal member 14 in position at internal opening 42 and retaining member 16 at external opening 44 with apparatus 10 in an implanted position. At this point, apparatus 10 is implanted and instrument 40 can advantageously be disengaged from rod 36 and removed in its entirety.

When apparatus 10 is to be removed, seal member 14 is deflated through tube 30 so as to position seal member 14 in the radially withdrawn position, and apparatus 10 may then be removed from urethra 38 as desired. Teeth 26, 28 hold the portions 22, 24 of body member 12 together during removal. For additional security during removal, instrument 40 could be inserted and engaged with rod 36 (or spokes 80, See FIG. 5) to further ensure that both portions 22, 24 are removed.

In further accordance with the invention, valve 18 is preferably provided having a structure which allows instrument 40 to pass therethrough for ease in engaging rod 36 during implantation. Alternatively, in one embodiment, structure is provided on valve 18 itself to perform the grippable function of rod 36.

Figure 3:
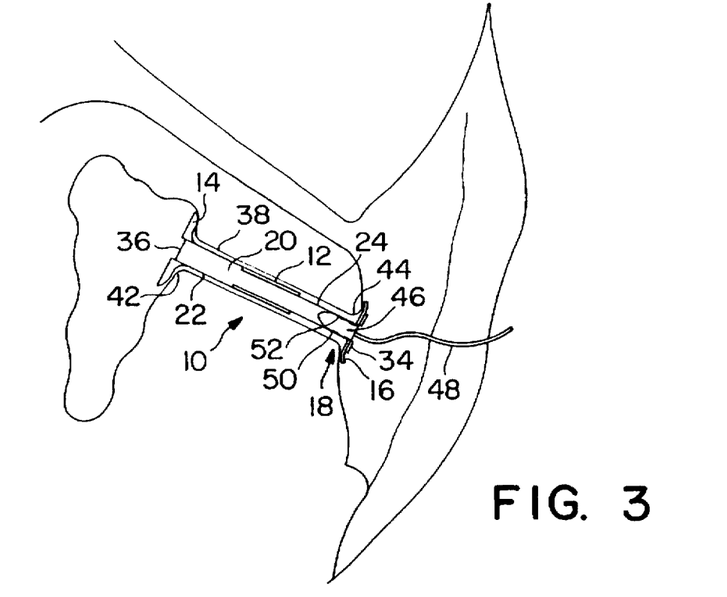
FIG. 3 is a side partially schematic view of an apparatus in accordance with the invention implanted for use in treating incontinence.

Referring now to FIG. 3, a simplified version of valve 18 is illustrated which calls for a plug member 46 which is removably positionable within passage 20, preferably near the proximal end of second tubular portion 24. Plug member 46 may suitably be provided with an attached cord member 48 or the like for ease in removal of same. Plug member 46 can readily be inserted to a position within passage 20 for substantially blocking flow therethrough, and can be removed as desired to allow flow through apparatus 10 without any risk of irritation or inflammation of the urethra or related tissues of the patient being treated. In accordance with this embodiment of the invention, tubular body member 12 and plug member 46 may preferably be provided with ridge or detent type structures 50 which engage with correspondingly-shaped structures 52 on plug member 46 so as to securely but releasably hold same in position. Of course, a wide variety of other configuration for plug member 46 could be provided in accordance with the invention.

Referring now to FIG. 4, a further embodiment of the invention is illustrated. In accordance with this embodiment, valve 18 has a plurality of deflectable prongs 19 resiliently biased toward the closed position as shown, and a valve actuating member 54 is provided in tubular body member 12 for opening valve 18 when desired. Valve actuating member 54 is preferably provided with a distally extending portion 56 which is positioned substantially adjacent to valve member 18, and a proximally located contact portion or hub 58. Valve actuating member 54 is preferably slidably positioned with respect to valve member 18 between a rest position as illustrated in FIG. 4 wherein distally extending portion 56 is at least partially spaced from valve member 18, and a distally biased position wherein distally extending portion 56 contacts valve member 18 so as to spread prongs 19 thereof and allow flow therethrough. In this regard, a flow passage 60 may suitably be defined within valve actuating member 54 and is preferably aligned with the opening structure of valve 18 to receive flow when desired. Still further in accordance with this embodiment, valve actuating member 54 may suitably have structure (not shown) for receiving a conduit or other vehicle for receiving flow through apparatus 10, preferably to a receptacle or location for disposal of same. Valve actuating member 54 is preferably biased toward the rest position, for example by a spring member 55.

Figures 5, 8:
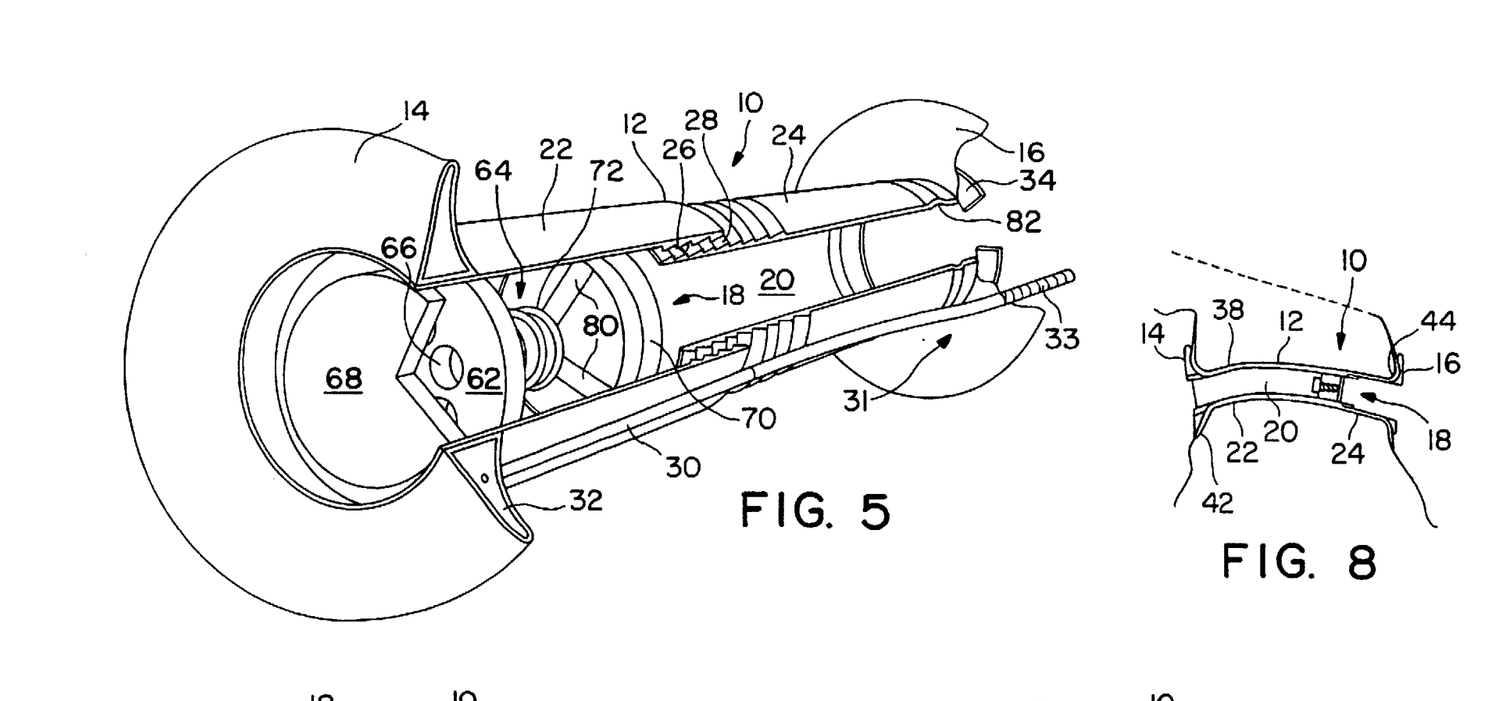
FIG. 5 is a perspective view of an alternative embodiment of the invention.
FIG. 8 is a side partially schematic view of a further alternative embodiment in accordance with the present invention.

Referring now to FIG. 5, a further alternative embodiment of valve member 18 in accordance with the invention will be described. In accordance with this embodiment of the invention, valve member 18 preferably includes a valve seat member 62 positioned in passage 20, and a valve body member 64 movably positioned with respect to valve seat member 62 between a closing or sealed position (See also FIG. 6), and an open position wherein flow through valve 18 is permitted (See FIG. 7). Valve seat member 62 is preferably a substantially disk-shaped member having a plurality of apertures 66 for allowing flow through valve seat member 62. Valve body 64 is preferably a substantially spool-shaped member having a disk-shaped head portion 68 positioned on the distal side of valve seat member 62, and preferably also including a proximally extending contact portion 70 extending proximally of the valve seat member 62. Valve body 64 in accordance with this embodiment is preferably biased proximally so as to sealably engage or contact head portion 68 with valve seat member 62 so as to cover or block apertures 66 and, thereby, block flow through valve seat member 62. Valve body member 64 is preferably biased into this closed position by a biasing member such as spring 72.

Still referring to FIG. 5, extending portion 70 is preferably also provided with a series of spokes 80 which serve the gripping function provided by rod 36 in the embodiment of FIGS. 1 and 4. In this embodiment, advantageously, valve member 18 is preferably mounted within first tubular portion 22 so that instrument 40 can grip or engage with spokes 80 to hold first tubular portion 22 in place while second tubular portion 24 with retaining member 16 thereon is positioned to the desired location. This configuration of valve member 18 including spokes 80 advantageously allows for implanting of apparatus 10 without needing to position or pass instrument 40 through valve member 18.

Figure 6:
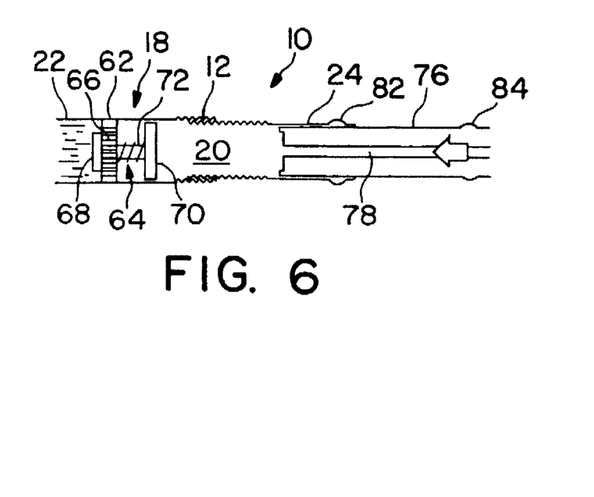
FIGS. 6 an 7 are side partially schematic views of the valve apparatus of the embodiment of FIG. 5.
Figure 7:
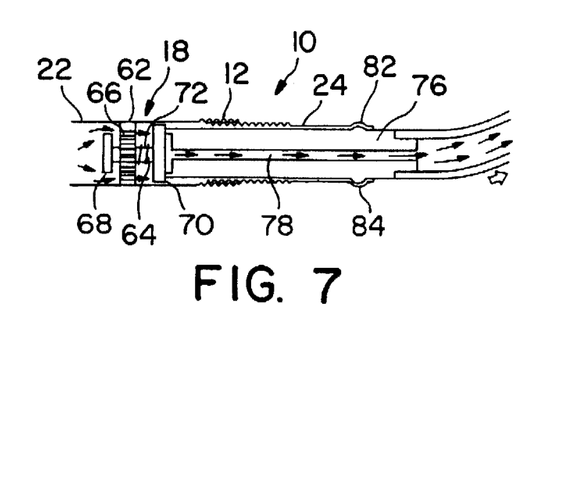

Referring now to FIGS. 6 and 7, the operation of valve 18 in accordance with the embodiment of FIG. 5 will be further discussed. FIG. 6 shows valve member 18 with head portion 68 substantially blocking apertures 66 of valve seat member 62. When desired, and advantageously, a conduit 76 is inserted into passage 20 so as to contact extending portion 70, and further insertion of conduit 76 serves to bias head portion 68 out of engagement with valve seat 62, thereby allowing flow through valve member 18 as shown in FIG. 7. As shown, conduit 76 preferably defines a flow passage 78 for receiving flow through valve 18 and conveying same to a suitable container or vessel for disposal (not shown). When flow through valve 18 is completed, removal of conduit 76 from passage 20 allows spring 72 to bias valve body 64 back into a closing or blocking position as shown in FIG. 6.

Still referring to FIGS. 5–7, it is also preferable that tubular body member 12 be provided with structure for releasably engaging a collection member or conduit 76 to hold same in place during flow through apparatus 10. Thus, as shown in the drawings, tubular body member 12 may be provided with an inwardly concave recess 82 while conduit 76 is provided with one or more radial projections 84 for releasable engagement with recess 82 as shown in FIG. 7. This feature would be advantageously combined with the embodiments of FIGS. 1 and 4 as well in accordance with the present invention.

Referring now to FIG. 8, a further alternative embodiment of the invention is illustrated wherein tubular body member 12 is at least partially flexible, and body member 12 may suitably be provided of material selected for this purpose. A portion or the entire length of body member 12 may suitably be provided of flexible material so as to advantageously allow tubular body member 12 to adapt to various curvature which may be encountered within urethra 38 as shown. This allows apparatus 10 to be further adaptable to various different physiology of patients to be treated. According to the invention, tubular body member 12 may be made of any flexible material compatible with the field of use of apparatus 10. Further, tubular body member 12 may be made of such flexible material in its entirety or only in pertinent portions where flexibility is desired.

In accordance with the foregoing, it should be readily apparent that there has been provided in accordance with the invention an apparatus for the treatment of incontinence, especially for treatment of incontinence in females, which is simple and effective in use, adaptable to a wide variety of applications, and significantly less likely to cause problems such as irritation, infection and the like.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

What is claimed is:

1. An apparatus for treating incontinence, comprising:
   a substantially tubular body member having a first end and a second end and defining a urine flow passage;
   an internal seal member positioned at the first end of the body member;
   an external retaining member positioned at the second end of the body member wherein the first end terminates in the internal seal member and the second end terminates in the external retaining member so as to define a total length of the body member between the internal seal member and the external retaining member, at least one member of the internal seal member and the external retaining member being moveable longitudinally with respect to the other member of the internal seal member and the retaining member;
   means for longitudinally securing the at least one member relative to the other member, whereby the tubular body member can be positioned in a urethra with the seal member substantially sealingly positioned in an interior opening of the urethra and with the retaining member positioned at an exterior opening of the urethra; and
   valve means positioned in the flow passage for controlling flow through the flow passage.

2. An apparatus according to claim 1, wherein the internal seal member comprises an inflatable collar for sealingly engaging with an internal opening of the urethra.

3. An apparatus according to claim 2, further comprising means for inflating the collar with the tubular body member positioned in the urethra.

4. An apparatus according to claim 3, wherein the means for inflating comprises an inflation fluid passage associated with the tubular body member and communicated at one end with the collar and having means at the other end for communicating with a source of inflation fluid for inflating the collar.

5. An apparatus according to claim 4, wherein the inflation fluid passage comprises a tube running lengthwise along the tubular body member.

6. An apparatus according to claim 5, wherein the tube extends through the retaining member.

7. An apparatus according to claim 1, wherein the tubular body member comprises a first body portion defining the first end and a second body portion defining the second end, and wherein the first body portion is longitudinally moveable relative to the second body portion whereby spacing between the seal member and the retaining member is adjustable.

8. An apparatus according to claim 7, further comprising means for locking the first body portion relative to the second body portion at a desired spacing.

9. An apparatus according to claim 8, wherein the means for locking comprises ratchet means associated with the first portion and the second portion for permitting relative movement of the first portion toward the second portion and for preventing relative movement of the first portion away from the second portion.

10. An apparatus according to claim 9, wherein the first portion comprises a first tubular element having a first set of ratchet teeth, and the second portion comprises a second tubular element having a second set of ratchet teeth for engaging the first set of ratchet teeth.

11. An apparatus according to claim 10, wherein the first portion has a first diameter and the second portion has a second diameter, and wherein the first and second diameter are selected so that one portion slidably fits within the other portion.

12. An apparatus according to claim 7, further comprising grippable means associated with the first tubular portion for gripping with an elongate object whereby the first tubular portion can be held in place during positioning of the second tubular portion relative to the first tubular portion.

13. An apparatus according to claim 12, wherein the grippable means comprises a rod positioned across at least a portion of the first end.

14. An apparatus according to claim 1, wherein the valve means comprises means for releasably blocking flow through the flow passage.

15. An apparatus according to claim 7, wherein the valve means comprises means for releasably blocking flow through the flow passage.

16. An apparatus according to claim 15, wherein the valve means is mounted within the first tubular portion and further comprises grippable means associated with the first tubular portion for gripping from a remote position whereby the first tubular portion can be held in place during positioning of the second tubular portion relative to the first tubular portion.

17. An apparatus according to claim 16, wherein the grippable means comprises at least one rod member mounted within the first tubular portion downstream of the valve means.

18. An apparatus according to claim 1, wherein the valve means comprises a valve seat positioned in the flow passage, and a valve body movably associated with the valve seat between a closing position wherein the valve body substantially sealingly engages the valve seat, and a flow position wherein the valve body does not engage the valve seat.

19. An apparatus according to claim 18, wherein the valve body is biased toward the closing position.

20. An apparatus according to claim 19, wherein the valve body extends through the valve seat toward the second end whereby a collection member can be inserted into the tubular body member from the second end so as to bias the valve body into the flow position.

21. An apparatus according to claim 1, wherein the valve means comprises a duck bill valve.

22. An apparatus according to claim 1 wherein the retaining member comprises a flange member arranged around the second end of the tubular body member.

23. An apparatus according to claim 1, further comprising means for releasably holding a collection member within the second end for receiving flow through the valve means.

24. An apparatus according to claim 1, wherein the tubular body portion is at least partially flexible whereby the tubular body portion can flex to adapt to a contour of the urethra.

25. An apparatus according to claim 1, wherein the valve means comprises a plug member releasably disposed within the flow passage.

26. A method for treating incontinence, comprising the steps of:

providing an apparatus comprising a substantially tubular body member having a first end and a second end and defining a urine flow passage, an internal seal member positioned at the first end, an external retaining member positioned at the second end of the body member, wherein the first end terminates in the internal seal member and the second end terminates in the external retaining member so as to define a total length of the body member between the internal seal member and the external retaining member, at least one member of the internal seal member and the external retaining member being moveable longitudinally with respect to the other member of the internal seal member and the retaining member, means for longitudinally securing the at least one member relative to the other member, whereby the tubular body member can be positioned in a urethra with the seal member substantially sealingly positioned in an interior opening of the urethra and with the retaining member positioned at an exterior opening of the urethra, and valve means positioned in the flow passage for controlling flow through the flow passage, wherein the internal seal member is positionable between a radially expanded position and a radially withdrawn position;

positioning the internal seal member in the radially withdrawn position;

inserting the apparatus into a urethra with the seal member extending beyond an internal opening of the urethra;

positioning the seal member in the radially expanded position;

moving the external retaining member relative to the seal member to an implanted position wherein the seal member substantially sealingly engages the internal opening of the urethra and the retaining member engages the external opening of the urethra;

securing the retaining member relative to the seal member in the implanted position; and selectively operating the valve means for controlling flow through the flow passage.

27. A method according to claim 26, further comprising the step of holding the seal member in place during the moving step.

28. A method according to claim 27, wherein the holding step comprises providing grippable means associated with the seal member; and gripping the grippable means from a remote position during the step of moving the retaining member relative to the seal member.

29. A method according to claim 28, wherein the gripping step comprises inserting a substantially elongate member through the tubular body to grip the grippable means during the step of moving the retaining member.

30. A method according to claim 26, wherein the valve means comprises a valve seat mounted in the tubular body and a valve body movably mounted relative to the valve seat between a closing position wherein the valve body substantially sealing engages the valve seat, and a flow position wherein the valve body does not engage the valve seat and wherein the step of selectively operating comprises the steps of moving the valve body toward the flow position to allow flow through the valve means and allowing the valve body to return to the closing position.

31. A method according to claim 30, wherein the step of moving the valve body comprises inserting a flow collecting member into the tubular body so as to push the valve body out of engagement with the valve seat whereby flow through the valve means enters the flow collecting member; and removing the flow collecting member from the tubular body whereby the valve body returns to the closing position.

32. An apparatus for treating incontinence, comprising:

a substantially tubular body member having a first end and a second end and defining a urine flow passage;

an internal seal member positioned at the first end of the body member;

an external retaining member positioned at the second end, at least one member of the internal seal member and the external retaining member being moveable longitudinally with respect to the other member of the internal seal member and the retaining member;

means for longitudinally securing the at least one member relative to the other member, whereby the tubular body member can be positioned in a urethra with the seal member substantially sealingly positioned in an interior opening of the urethra and with the retaining member positioned at an exterior opening of the urethra; and valve means positioned in the flow passage for controlling flow through the flow passage, wherein the tubular body member comprises a first body portion defining the first end and a first portion of the flow passage, and a second body portion defining the second end and a second portion of the flow passage, and wherein the first body portion is longitudinally movable relative to the second body portion whereby spacing between the seal member and the retaining member is adjustable.

33. An apparatus for treating incontinence, comprising:

a substantially tubular body member having a first end and a second end and defining a urine flow passage;

an internal seal member positioned at the first end of the body member;

an external retaining member positioned at the second end, at least one member of the internal seal member and the external retaining member being moveable longitudinally with respect to the other member of the internal seal member and the retaining member;

means for longitudinally securing the at least one member relative to the other member, whereby the tubular body member can be positioned in a urethra with the seal member substantially sealingly positioned in an interior opening of the urethra and with the retaining member positioned at an exterior opening of the urethra; and valve means positioned in the flow passage for controlling flow through the flow passage wherein the tubular body member comprises a first body portion defining the first end and a second body portion defining the second end, wherein the first body portion is longitudinally movable relative to the second body portion whereby spacing between the seal member and the retaining member is adjustable, and further comprising means for locking the first body portion relative to the second body portion at a desired spacing, said means for locking comprising a first set of ratchet teeth positioned on said first portion and skewed toward the first end, and a second set of ratchet teeth positioned on the second portion and skewed toward the second end, whereby relative movement of the first portion toward the second portion is permitted, and relative movement of the first portion away from the second portion is prevented.

34. An apparatus for treating incontinence, comprising:

a substantially tubular body member having a first end and a second end and defining a urine flow passage;

an internal seal member positioned at the first end of the body member;

an external retaining member positioned at the second end, at least one member of the internal seal member and the external retaining member being moveable longitudinally with respect to the other member of the internal seal member and the retaining member;

means for longitudinally securing the at least one member relative to the other member, whereby the tubular body member can be positioned in a urethra with the seal member substantially sealingly positioned in an interior opening of the urethra and with the retaining member positioned at an exterior opening of the urethra; and valve means positioned in the flow passage for controlling flow through the flow passage, wherein the tubular body member comprises a first body portion defining the first end and a second body portion defining the second end, wherein the first body portion is longitudinally movable relative to the second body portion whereby spacing between the sealed member and the retaining member is adjustable, and further comprising grippable means within the first tubular portion for gripping with an elongate object whereby the first tubular portion can be held in place during positioning of the second tubular portion relative to the first tubular portion.

35. An apparatus for treating incontinence, comprising:

a substantially tubular body member having a first end and a second end and defining a urine flow passage;

an internal seal member positioned at the first end of the body member;

an external retaining member positioned at the second end, at least one member of the internal seal member and the external retaining member being moveable longitudinally with respect to the other member of the internal seal member and the retaining member;

means for longitudinally securing the at least one member relative to the other member, whereby the tubular body member can be positioned in a urethra with the seal member substantially sealingly positioned in an interior opening of the urethra and with the retaining member positioned at an exterior opening of the urethra; and valve means positioned in the flow passage for controlling flow through the flow passage, wherein the tubular body member comprises a first body portion defining the first end and a second body portion defining the second end, and wherein the first body portion is longitudinally movable relative to the second body portion whereby spacing between the seal member and the retaining member is adjustable, wherein the valve means comprises means for releasably blocking flow through the flow passage mounted within the first tubular portion, and further comprising grippable means within the first tubular portion for gripping from a remote position whereby the first tubular portion can be held in place during positioning of the second tubular portion relative to the first tubular portion.

36. An apparatus for treating incontinence, comprising:

a substantially tubular body member having a first end and a second end and defining a urine flow passage;

an internal seal member positioned at the first end of the body member;

an external retaining member positioned at the second end, at least one member of the internal seal member and the external retaining member being moveable longitudinally with respect to the other member of the internal seal member and the retaining member;

means for longitudinally securing the at least one member relative to the other member, whereby the tubular body member can be positioned in a urethra with the seal member substantially sealingly positioned in an interior opening of the urethra and with the retaining member positioned at an exterior opening of the urethra; and valve means positioned in the flow passage for controlling flow through the flow passage, wherein the valve means comprises a valve seat positioned in the flow passage, and a valve body movably associated with the valve seat between a closing position wherein the valve body substantially sealingly engages the valve seat, and a flow position wherein the valve body does not engage the valve seat, the valve body being biased toward the closing position, and wherein the valve body extends through the valve seat toward the second end whereby a collection member can be inserted into the tubular member from the second end so as to bias the valve body into the flow position.

37. An apparatus for treating incontinence, comprising:

a substantially tubular body member having a first end and a second end and defining a urine flow passage;

an internal seal member positioned at the first end of the body member;

an external retaining member positioned at the second end, at least one member of the internal seal member and the external retaining member being moveable longitudinally with respect to the other member of the internal seal member and the retaining member;

means for longitudinally securing the at least one member relative to the other member, whereby the tubular body member can be positioned in a urethra with the seal member substantially sealingly positioned in an interior opening of the urethra and with the retaining member positioned at an exterior opening of the urethra;

valve means positioned in the flow passage for controlling flow through the flow passage;

means for releasably holding a collection member within the second end for receiving flow through the valve means.

38. A method for treating incontinence, comprising the steps of:

providing an apparatus comprising a substantially tubular body member having a first end and a second end and defining a urine flow passage, an internal seal member positioned at the first end, grippable means fixedly associated with the seal member, and an external retaining member positioned at the second end, at least one member of the internal seal member and the external retaining member being moveable longitudinally with respect to the other member of the internal seal member and the retaining member, means for longitudinally securing the at least one member relative to the other member, whereby the tubular body member can be positioned in a urethra with the seal member substantially sealingly positioned in an interior opening of the urethra and with the retaining member positioned at an exterior opening of the urethra, and valve means positioned in the flow passage for controlling flow through the flow passage, wherein the internal seal member is positionable between a radially expanded position and a radially withdrawn position;

positioning the internal seal member in the radially withdrawn position;

inserting the apparatus into a urethra with the seal member extending beyond an internal opening of the urethra;

positioning the seal member in the radially expanded position;

moving the external retaining member relative to the seal member to an implanted position wherein the seal member substantially sealingly engages the internal opening of the urethra and the retaining member engages the external opening of the urethra;

holding the seal member in place during the moving step by gripping the grippable means from a remote position during the step of moving the retaining member relative to the seal member;

securing the retaining member relative to the seal member in the implanted position; and selectively operating the valve means for controlling flow through the flow passage.

39. A method for treating incontinence, comprising the steps of:

providing an apparatus comprising a substantially tubular body member having a first end and a second end and defining a urine flow passage, an internal seal member positioned at the first end, an external retaining member positioned at the second end, at least one member of the internal seal member and the external retaining member being moveable longitudinally with respect to the other member of the internal seal member and the retaining member, means for longitudinally securing the at least one member relative to the other member, whereby the tubular body member can be positioned in a urethra with the seal member substantially sealingly positioned in an interior opening of the urethra and with the retaining member positioned at an exterior opening of the urethra, and valve means positioned in the flow passage for controlling flow through the flow passage, wherein the internal seal member is positionable between a radially expanded position and a radially withdrawn position;

positioning the internal seal member in the radially withdrawn position;

inserting the apparatus into a urethra with the seal member extending beyond an internal opening of the urethra;

positioning the seal member in the radially expanded position;

moving the external retaining member relative to the seal member to an implanted position wherein the seal member substantially sealingly engages the internal opening of the urethra and the retaining member engages the external opening of the urethra;

securing the retaining member relative to the seal member in the implanted position; and selectively operating the valve means for controlling flow through the flow passage, wherein the valve means comprising a valve seat mounted in the tubular body and a valve body movably mounted relative to the valve set between a closing position wherein the valve body substantially sealingly engages the valve seat, and a flow position wherein the valve body does not engage the valve seat, and wherein the step of selectively operating comprises the steps of moving the valve body toward the flow position to allow flow through the valve means and allowing the valve body to return to the closing position, and wherein the step of moving the valve body comprises inserting a flow collecting member into the tubular body so as to push the valve body out of engagement with the valve seat whereby flow through the valve means enters the flow collecting member, and removing the flow collecting member from the tubular body whereby the valve body returns to the closing position.

* * * * *